United States Patent
Rempe et al.

[11] Patent Number: 6,041,448
[45] Date of Patent: Mar. 28, 2000

[54] URINE EVACUATOR

[76] Inventors: Kristin K. Rempe, 2089 Kingston; Sandra L. Fitzpatrick, 9673 Bonnie Briar, both of White Lake, Mich. 48386

[21] Appl. No.: 09/121,918
[22] Filed: Jul. 24, 1998

Related U.S. Application Data
[60] Provisional application No. 60/053,647, Jul. 24, 1997.

[51] Int. Cl.⁷ .................................................. A47K 11/00
[52] U.S. Cl. .......................................... 4/144.1; 479/144.3
[58] Field of Search ................................ 4/144.1, 144.3, 4/144.2, 144.4, 458, 114.1, 476, 479

[56]        References Cited
         U.S. PATENT DOCUMENTS

| | | | |
|---|---|---|---|
| 1,148,897 | 8/1915 | Hayes | 4/114.1 |
| 3,131,403 | 5/1964 | Hill | 4/144.3 |
| 4,202,058 | 5/1980 | Anderson | 4/144.3 |
| 5,632,736 | 5/1997 | Block | 4/144.3 |
| 5,852,830 | 12/1998 | Horn | 4/144.1 |

*Primary Examiner*—David J. Walczak
*Attorney, Agent, or Firm*—Weintraub & Brady, P.C.

[57] ABSTRACT

A urine evacuation device, or evacuator, includes a generally bulbous guard member having an opening form therein and to which urine is directed. An elongated tubular member preferably, accordion pleated, is secured at one end thereof to and is in registry with the opening formed in the guard member. The opposite, or free end, of the tubular member has a cap removably affixed thereto to trap urine collected within the tubular member. The device may include clips, snaps or other appropriate devices to secure the evacuator to either an under garment or around the body or torso of a user.

4 Claims, 1 Drawing Sheet

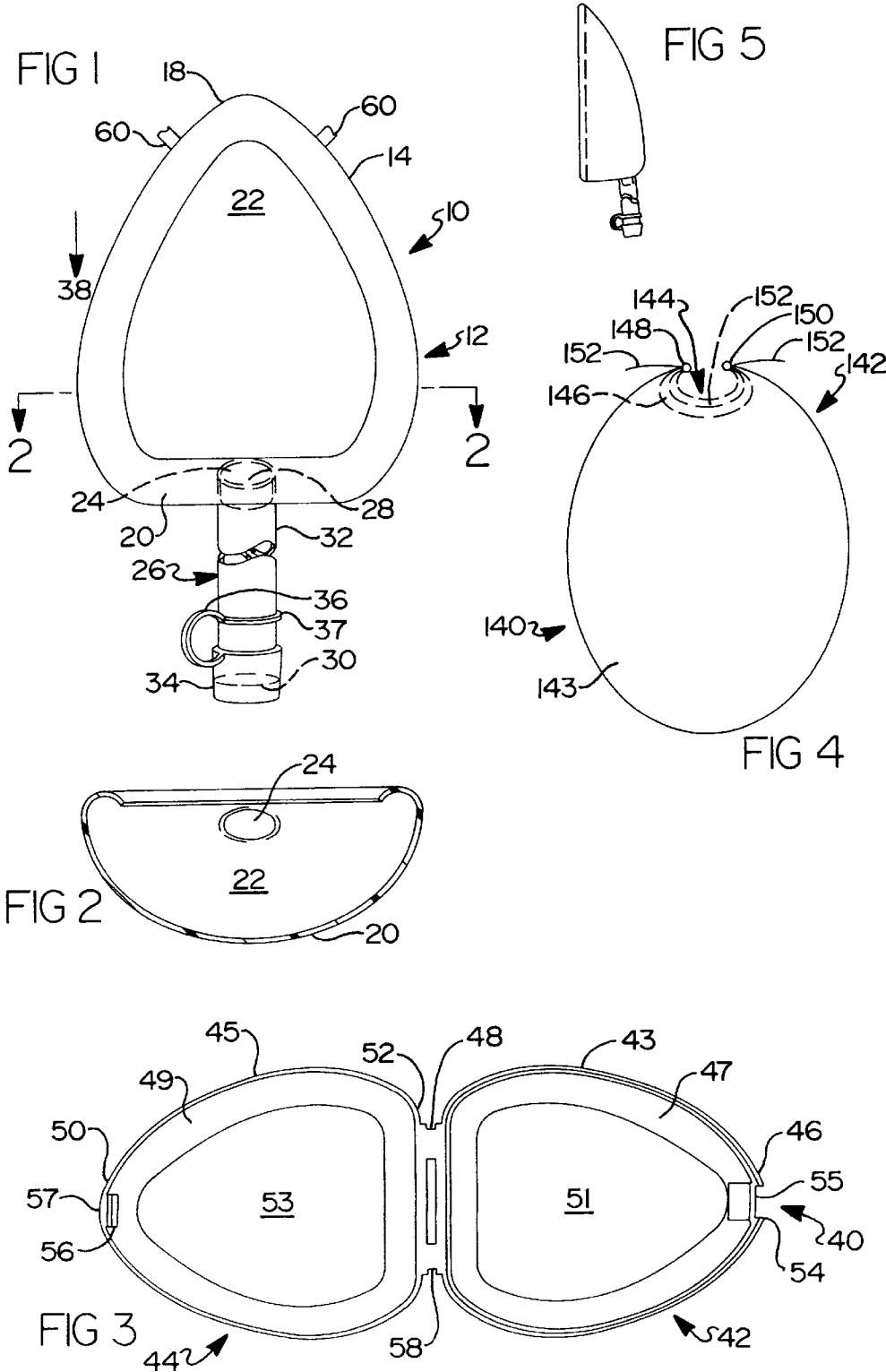

URINE EVACUATOR

CROSS REFERENCE TO RELATED APPLICATION

This application is a completion application of co-pending U.S. Provisional application Ser. No. 60/053,647 for "Urine Evacuator" filed Jul. 24, 1997, the disclosure of which is hereby incorporated by reference.

STATEMENT REGARDING FEDERALLY FUNDED RESEARCH

Not applicable.

BACKGROUND OF THE INVENTION

1. Field of the Invention

The present invention concerns urine evacuator devices. More particularly, the present invention concerns portable urine evacuator devices.

2. Prior Art

As is known to those skilled in the art to which the present invention pertains, urine evacuation during activities remote from bathroom facilities is not only inconvenient but, at times, depending on the circumstances inappropriate. Therefore, it is apparent that the existence of a device which enables urination without the removal of garments, is highly desirable. It is to be noted that the art has, previously, addressed this need. For example, U.S. Pat. No. 5,243,712 discloses a disposable urinary device for use by females which comprises a pleated or collapsible and extensible funnel-shaped body having positioning loops. The device includes an exiting end which is open and which directs urine outwardly without touching garments, In U.S. Pat. No. 4,892,527 there is disclosed a sportsman's reusable anti-collapsing urine collection device which includes a pouch which secures, or holsters, about the leg of the user.

Other devices include that disclosed in U.S. Pat. No. 5,333,330 which defines a disposable device formed of paper, etc. The device includes a tubular element provided with accordion pleats for (collapsing and extension of the tubular member through which urine is discharged.

Other art includes that found in U.S. Pat. Nos. 4,476,879, 5,401,263 and 5,330,453.

It is to be appreciated from the above that the art does not necessarily abide the storage and collection of the urine until it is appropriate to discharge same from a collector. Moreover, the prior art does not provide a simple storage device for transporting the collection device. As detailed herein below, the present invention addresses these concerns.

SUMMARY OF THE INVENTION

In accordance with the present invention, there is provided a urine evacuation device or a urine evacuator which, generally, comprises a guard member defined by a concave, bulbous wall and which is substantially ovular in shape. The device further includes a tubular member defined by a elongated hollow body having a first open end and a second opposite open end. The tubular member is, preferably, accordion pleated to enable it be compacted and/or extended and is used as a collection device for urine. The second, or free end of the tubular member is fitted with a closure member, such as a cap or the like. The first end of the tubular member is in communication with the bulbous wall and is disposed at a position appropriate such that urine impacting against the bulbous wall is directed downwardly into the tubular member.

The device may further include means for securing the evacuator to clothing or about the torso of the user.

For a more complete understanding of the present invention, reference is made to the following detail description and accompanying drawing. In the drawing like reference characters refer to like parts throughout the several views in which:

BRIEF DESCRIPTION OF THE DRAWINGS

FIG. 1 is a top view of a urine evacuator in accordance with the present invention;

FIG. 2 is a cross sectional view of the evacuator taken along line 2—2 of FIG. 1;

FIG. 3 is a top view of a first embodiment of a carrying device for use with the urine evacuator hereof;

FIG. 4 is a top view of a second embodiment of a carrying device for use with the urine evacuator hereof;

FIG. 5 is a side view of the urine evacuator hereof.

DETAILED DESCRIPTION OF THE PREFERRED EMBODIMENT

As noted herein above and at the outset, it is to be noted that the present invention is particularly adapted to be used during athletic activities and at other times in which it is inconvenient and/or inappropriate to remove or open garments in order to urinate by both men and women. The present invention, as detailed below, enables a convenient and sanitary way to urinate without the need to remove or open garments.

Now and with reference to the drawing and, in particular, FIGS. 1 and 2, there is shown a urine evacuator device in accordance with the present invention and which is depicted, generally, at 10. The evacuator 10 defines a guard member 12 which comprises a concave, bulbous wall 22 terminating in a top perimetral edge 14, the edge 14 being substantially in the shape of an oval, as shown. The wall 22 has a narrow end 18 and a broad end 20. The wall 22 cooperates with the perimetral edge 14 to form an open-topped unitary vessel. In use, the edge 14 contacts with and assures proper emplacement of the evacuator 10 against the genital area of a person, as described herein below. The guard member 12 is, preferably, made of a pliable, non-porous hygienic material such as a silicone plastic or the like.

As shown in the drawing, an aperture 24 is formed in the wall 22 at any convenient location and is, preferably, provided in the region of the broad end 20. The aperture 24 provides communication between the wall 22 and a tubular member 26 as described herein below.

The device 10 further comprises the tubular member 26. The tubular member 26 is an elongated hollow body 32 having a first open end 28 and a second, opposite open end 30. The diameter of the first open end 28 is, preferably, substantially equal to the diameter of the aperture 24 in the wall 22. However, the diameter may be larger or smaller than the aperture 24, as desired.

The first open end 28 of the tubular member 26 is in registry with the aperture 24 and is connected with the guard member 12 thereat by any convenient means, such as by being integrally formed with the guard member 12, or by being friction fitted in a sealed manner to the guard member, by sonic welding, gluing, or the like.

The device 10 may, also, include a cap 34 that is sized to provide sealing closure for the second open end 30 of the tubular member 26. A stem 36 is, preferably, formed integrally with the cap 34 and extends therefrom. The stem 36 has an aperture 37 formed therethrough. The body 32 of the tubular member 26 is disposed within the aperture 37 in the stem 36 so the cap is not lost.

The hollow body 32 is made of a flexible, natural material, such as a soft plastic or the like. Preferably, the tubular member 26 is an accordion pleated body 32 having a plurality of hinged or accordion edges along the length thereof to enable extension and collapse thereof, to enable collection of large volumes of urine during use and easier storage and transportation between uses. The internal volume of the hollow body 32 is sufficient to hold an appropriate volume of fluid. This is accomplished by a combination of the dimensions of the body 32 and the extensibility of the body due to its material of construction.

The present invention may, also, include means 60 for holding the guard member 12 in place after placement against a person, such as a clip attached to the guard member 12 at the narrow end 18 thereof which may secure the device to an undergarment (not shown). The clip may be attached to the guard member 12 by any convenient means, such as riveting, etc. Similarly, means for attachment such as snaps (not shown), etc. may be used. In use, a user would clip the device 10 to a belt or clothing the user is wearing.

It is also possible to incorporate a belt into the device hereof to define the means 60 for holding the device 10 in place. The belt (not shown) may be attached to the guard member 12 at the narrow end thereof or any other suitable location by any convenient means. Similarly, the device 10 may be held in place by the friction of an undergarment which enshrouds the device.

The present invention also contemplates a carrying device 40 for transporting the device 10. The carrying device, or means for carrying, is sufficiently sized and shaped to enable removable emplacement of the device 10 therewithin. The carrying device may be of any desired configuration. For example, and as shown in FIG. 3, the carrying device 40 may be a clam-shell-type carrying case.

The carrying device 40 has a first member 42 and a second member 44. The first member 42 has a side wall 47 terminating in an edge 43, the edge 43 being substantially similarly shaped to the perimetral edge 14 of the guard member 12 but being both longer and wider than the device 10. The first member 42 has a narrow end 46 and a broad end 48. A bottom wall 51 is integrally formed with the side wall 47, thus providing a closed-bottom first member 42.

The second member 44 is substantially a mirror image of the first member 42 and has a side wall 49 terminating in an edge 45, the edge 45 being substantially similarly shaped to the edge 43 of the first member 42. The second member 44 has a narrow end 50 and a broad end 52. A bottom wall 53 is integrally formed with the side wall 49, thus providing a closed-bottom second member 44.

The combined heights of the side walls 47 and 49 are at least slightly greater than the height of the side wall 22 of the guard member 12.

The first and second members 42 and 44, respectively, are connected by any suitable means that allows movement of the two members toward and away from each other, such as at least one flexible flap formed integrally with both the first and the second member 42 and 44, a hinge (not shown), or the like.

The carrying case 40 is closed by any convenient means for closing. One such means for closing may be defined by providing a depression 54 formed in the side wall 47 of the first member 42 at its narrow end 46 which cooperates with a lip 55 disposed on the first member 42 proximate the depression 54. The second member 44 has a flange 56 disposed at the narrow end 50 and integrally formed therewith. The flange 56 has a shoulder 57 which seats against the lip 55, thus enabling closure to the carrying case 40. Other convenient means for closing, such as snaps, etc. may be used.

Because the heights of the two side walls 47 and 49 combine to exceed the height of the side wall 22 of the guard member 12, when the first and second members 42 and 44 of the carrying case 40 are closed, the carrying case 40 provides a hollow interior of a sufficient size to store the device 10.

In a second embodiment of the means for carrying, and as shown in FIG. 4, a carrying case 140 for the device 10 comprises a soft-sided pouch 142. The pouch 142 has a wall 143 with an first aperture 144 formed therethrough. A channel 146 is formed in the wall 143 surrounding the first aperture 144, the channel terminating in second and third apertures 148 and 150. A draw string 152 is threaded into the second aperture 148, through the channel 146, and out the third aperture 150. To store the device 10, the device 10 is emplaced into the pouch 142 through the first aperture 144, then the draw string 152 is pulled to close the pouch 142.

In use, the device 10 is first removed from the carrying case 40 or 140, if a carrying case has been used. Next the cap 34 is mounted onto the tubular member 26 over the second open end 30 to seal it. The guard member 12 is then emplaced in proximity to the urinary area of a person and oriented such that the perimetral edge 14 is placed against the skin of the person with the broad end 20 of the top edge 14 positioned in a downward position, as depicted in the direction of arrow 38. When urination occurs, the urine hits against the wall 22. Gravity pulls the urine downwardly, in the direction of the arrow 38. When the urine reaches the aperture 24, the urine drains through the aperture 24, through the first open end 28 of the tubular member 26, and into the hollow interior of the body 32 of the tubular member 26, where it is collected. The urine is entrapped within the body 32 by the cap 34, which seals the second open end 30. The tubular member may be extended to enable collection of volumes of urine.

When urination is complete, or at such later time as is convenient for the person, such as at the end of an activity as discussed hereinbelow, the user removes the device 10 from her person. The device 10 may, then, be either disposed of or retained for re-use. If the device 10 is retained for re-use, the cap 34 is removed from the second open end 30, thus allowing the urine to drain out of the body 32 of the tubular member 26.

It is to be appreciated that the device 10 provides utility to any person who does not wish to remove or open any garments in order to urinate. The guard member 12 is simply emplaced in proximity to the person's urinary area. It is envisioned that the present invention will be particularly useful to skiers, snowmobilers, golfers, and others who have to urinate outdoors while encased in multiple layers of clothing, though it is envisioned that the present invention will be useful in many other environments as well. Similarly, the device hereof may be used by incontinent persons who cannot conveniently be in proximity to bathroom facilities at all times.

While the invention has been illustrated and described in detail in the drawings and the foregoing description, the same is to be considered as illustrative and not restrictive in character, it being understood that only the preferred embodiments have been shown and described fully and that all changes and modifications that come within the spirit of the invention are desired to be protected.

Having, thus, described the invention what is claimed is:

1. A urine evacuator adapted for extended temporary storage of urine, comprising:
   a) a guard member comprising a substantially ovular bulbous concave wall, having an opening formed therein,
   b) a body engaging perimetal edge circumferentially disposed about and integral with the wall,
   c) a tubular member having a first end in registry with the opening, the tubular member being secured to the guard member and disposed about the opening, the tubular member having a second end opposite the first end, the tubular member having an accordion pleated body which can be extended to provide an increased volume for the collection and temporary storage of urine and
   d) a cap for sealingly closing the second end of the tubular member.

2. The evacuator of claim 1 which further comprises: means for holding the guard member in place against the user's body for temporary extended use and storage.

3. The evacuator of claim 1 further comprising:
   a carrying case for the evacuator.

4. The evacuater of claim 3 wherein the carrying case comprises:
   a) a first member and a second member, the members being mirror images of each other,
   b) a hinge interconnecting the first and second members; and
      wherein the first and second members each have the same configuration as the perimetal edge of the guard member.

* * * * *